United States Patent
Balestrieri

(10) Patent No.: US 9,902,795 B2
(45) Date of Patent: Feb. 27, 2018

(54) METHOD FOR PREPARING A HYDROGEL THROUGH THE USE OF ALKOXYDES, THE PRODUCT THUS OBTAINED AND THE USE THEREOF

(75) Inventor: Gerardo Balestrieri, Milan (IT)

(73) Assignee: PHARMAFILL SRL, Mariano Comense (IT)

( * ) Notice: Subject to any disclaimer, the term of this patent is extended or adjusted under 35 U.S.C. 154(b) by 537 days.

(21) Appl. No.: 12/447,555

(22) PCT Filed: Sep. 17, 2007

(86) PCT No.: PCT/IB2007/002809
§ 371 (c)(1),
(2), (4) Date: Oct. 20, 2009

(87) PCT Pub. No.: WO2008/053289
PCT Pub. Date: May 8, 2008

(65) Prior Publication Data
US 2010/0099812 A1    Apr. 22, 2010

(30) Foreign Application Priority Data
Nov. 3, 2006 (IT) ............................. NO2006A0012

(51) Int. Cl.
C08L 29/04 (2006.01)
C08L 67/00 (2006.01)
A61K 9/00 (2006.01)
A61F 2/02 (2006.01)
C08F 261/04 (2006.01)
A61L 27/16 (2006.01)
A61L 27/52 (2006.01)
C08J 3/075 (2006.01)
C08F 8/30 (2006.01)

(52) U.S. Cl.
CPC ............ C08F 261/04 (2013.01); A61L 27/16 (2013.01); A61L 27/52 (2013.01); C08F 8/30 (2013.01); C08J 3/075 (2013.01); C08F 2810/20 (2013.01); C08F 2810/30 (2013.01); C08J 2329/04 (2013.01)

(58) Field of Classification Search
USPC ........ 524/804, 35, 916; 523/105; 525/11, 57
See application file for complete search history.

(56) References Cited

U.S. PATENT DOCUMENTS

| | | | | |
|---|---|---|---|---|
| 2,394,776 A | * | 2/1946 | Hoffman et al. | ............... 525/59 |
| RE32,649 E | * | 4/1988 | Brandt et al. | ................. 604/368 |
| 4,781,838 A | * | 11/1988 | Crassous | ............... A61K 35/16 |
| | | | | 210/502.1 |
| 4,874,500 A | * | 10/1989 | Madou | ................. G01N 27/403 |
| | | | | 204/408 |
| 5,880,216 A | * | 3/1999 | Tanihara et al. | ................. 525/61 |
| 6,007,712 A | * | 12/1999 | Tanaka et al. | ................. 210/151 |
| 6,615,078 B1 | * | 9/2003 | Burson | .................... A61N 1/30 |
| | | | | 600/345 |
| 7,169,847 B2 | | 1/2007 | Solomon et al. | |
| 2005/0009994 A1 | | 1/2005 | Solomon et al. | |
| 2005/0106256 A1 | * | 5/2005 | Hung et al. | .................. 424/488 |
| 2006/0079597 A1 | * | 4/2006 | Muratoglu | ................. C08J 3/28 |
| | | | | 522/178 |
| 2006/0227330 A1 | * | 10/2006 | Hjelme | ................. G01N 21/45 |
| | | | | 356/481 |
| 2008/0140037 A1 | | 6/2008 | Newman | |
| 2009/0053313 A1 | | 2/2009 | Protopapa et al. | |

FOREIGN PATENT DOCUMENTS

| | | | |
|---|---|---|---|
| CN | 1793191 A | | 6/2006 |
| EP | 1637547 A | | 3/2006 |
| JP | 355142075 A | * | 11/1980 |
| KR | 100443165 B1 | | 7/2004 |
| WO | 02068100 A | | 9/2002 |
| WO | 2006062609 A | | 6/2006 |

* cited by examiner

Primary Examiner — Tae H Yoon
(74) Attorney, Agent, or Firm — Pearne & Gordon LLP

(57) ABSTRACT

A process for the preparation of a completely biocompatible and reabsorbable hydrogel, through the use of alkoxides of polymers and/or resins containing hydroxyl functions. The invention also relates to the hydrogel obtainable with the method and uses thereof. In particular, the invention relates to the use of the hydrogel for the preparation of an injectable filler for correcting and/or treating different types of tissue deficits.

7 Claims, No Drawings

METHOD FOR PREPARING A HYDROGEL THROUGH THE USE OF ALKOXYDES, THE PRODUCT THUS OBTAINED AND THE USE THEREOF

This application is a National Stage Application of International Patent Application No. PCT/IB2007/002809, filed on Sep. 17, 2007, and claims the benefit of Italian Patent Application No. NO2006A000012, filed on Nov. 3, 2006, all of which are incorporated herein by reference in their entirety.

FIELD OF THE INVENTION

The present invention relates to a process for the preparation of a completely biocompatible hydrogel, through the use of alkoxides of polymers and/or hydroxyl functions containing resins. The invention also relates to the hydrogel obtainable with said method and uses thereof.

In particular, the invention relates to the use of said hydrogel for the preparation of a degradable injectable filler for correcting and/or treating different types of tissue deficits.

BACKGROUND ART

Various processes for the preparation of hydrogels are known, both with synthetic products, such as for example polymers and/or resins, and with natural products such as, for example, collagen.

In the particular case of synthetic hydrogels, those currently on the market are carried out, on average, through polimerization and cross-linking (namely, coupling between polymers and monomers) of two or more types of monomers in a random way.

As a main component of the above monomers, acrylamide is very often used. This substance, at a monomer level, is notoriously carcinogenic and, also with the presence of small non-polymerized residues, can create such health problems that in some States its use has been forbidden.

In fact, even if it is possible to subject final hydrogels to an opportune wash, the thick mass of the hydrogel does not allow a homogeneous penetration of the washing solution and, therefore, does not ensure the complete removal of starting monomers and/or oligomers (particularly dimers) which can be formed during the preparation process of the hydrogel.

Finally, it is often not possible to ensure the complete removal of other reagents (for example metals, catalysts, and so on) which usually are employed during the preparation of the hydrogel itself.

Also hydrogels formed through UV rays, gamma rays or with a freeze-thaw system are known, but these procedures give rise to changes of a physical and not chemical nature and for this reason they do not generally ensure any guarantee of stability over time, especially if hydrogels have to be stored in the presence of a high quantity of water, as in the present case.

Furthermore, there exist hydrogels based on raw materials of animal or vegetal origin, whose mean life is however very moderate. Moreover, in case of hydrogels of animal origin, the compatibility of these products with subjects on which one intends to carry out the treatment has generally to be ascertained.

There remains therefore a strong need of being able to provide hydrogels which are: injectable; completely biocompatible and free of residues and/or impurities resulting from their preparation reaction; bioreabsorbable in varying times and reproducible depending on the type of the intended use; having such homogeneity and regularity features in the whole structure that the behaviour towards the organism is advantageous.

The object of the present invention is to provide an adequate answer to the need above pointed out.

SUMMARY OF THE INVENTION

This and other aims, which will result apparent from the following detailed description, have been attained by the Applicant, which has found that, by reacting in an aqueous basic environment a polymer containing hydroxyl functions with at least a compound containing at least two double bonds, it is possible to give said answer to the problems above described.

Therefore, a process for the preparation of a non-toxic and biocompatible hydrogel forms an object of the present invention, as reported in the appended independent claim.

Another object of the present invention is the above hydrogel, whose features are reported in the appended independent claim.

A further object of the present invention is the use of said hydrogel, as reported in the appended independent claim.

Preferred embodiments of this invention are reported in the appended dependent claims.

DETAILED DESCRIPTION OF THE INVENTION

An object of the present invention is a process for the preparation of a completely non-toxic and biocompatible hydrogel, including at least a first step in which at least a polymer and/or a copolymer containing a number of hydroxyl functions is reacted with at least a compound containing at least two carbon-carbon double bonds, in an aqueous basic environment, to give the desired cross-linked hydrogel, in which the cross-linking takes place through the formation of ether bonds between the hydroxyl groups of said polymer and/or a copolymer and the double bonds of said at least one monomer.

Preferably, said polymers and/or copolymers containing said hydroxyl functions are selected from: polyvinyl alcohol and/or derivatives thereof, polyallyl alcohol and/or derivatives thereof, ethers and/or esters of resins with —OH groups, polyvinylethylene alcohols and analogues, such as polyglycol derivatives, polyethylene glycol resins, polysaccharides (for example, dextran, starch, chondroitin sulphate, amylose), polypeptides and so on.

Among these, polyvinyl alcohol (in short, PVOH) has resulted to be particularly preferred.

In an exemplificative embodiment, said polyvinyl alcohol is a completely hydrolized polyvinyl alcohol (wherein whit this term is commonly meant a PVOH having a hydrolysis degree ≥98%; preferably, ≥99%). Preferably, compounds containing at least two carbon-carbon double bonds, >C=C<, are selected from: diacrylates, polyethylene glycol diacrylate, glycerol 1,3-diglycerolate diacrylate; bisacrylamides, methylenebisacrylamide, ethylenebisacrylamide, isopropylenbisacrylamide; diallyl urea; general dienes (such as, for example, isoprene, butadiene) and derivatives thereof.

Said above compounds are generally referred as "monomers" containing at least a pair of carbon-carbon double bonds, >C=C<.

The fact of having at least a pair of double bonds >C=C< allows said monomers above mentioned to bind, in the experimental conditions foreseen by the process of the present invention, to OH groups of the polymer/s above mentioned by forming inter-chain junction points along all the polymeric chain, thus creating a three-dimensional net which retains a remarkable quantity of water.

The reaction environment consists of the aqueous solution of a strong base. It can be of an organic or inorganic type and, depending on the base used, quantities, times and temperatures can vary, without prejudice to the reactive principle in object.

An aqueous NaOH solution has resulted particularly preferred.

In the exemplificative case later stated, a NaOH solution has been used.

In the aqueous basic conditions of the present invention, at least a part of OH groups of the above polymers are transformed in alkoxides, which quickly and quantitatively react with the double bonds of the monomers above described, forming a series of ether covalent stable bonds, —O—.

It is known in the art that, as a rule, alkoxides of this type are obtained only through a reaction between an alcohol and sodium (or a metallic iodide) in a non-aqueous environment; this reaction irreversibly proceeds by forming a solid metallic alkoxide, which can also be isolated.

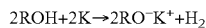
2ROH+2K→2RO⁻K⁺+H₂

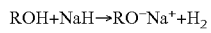
ROH+NaH→RO⁻Na⁺+H₂

Alcohol metal salts are strong bases and constitute real reagents.

However, the use of said alcohol metal salts is possible in a non-aqueous reaction environment.

In fact, as a rule, it is not possible to transform an alcohol in the corresponding alkoxide with NaOH in an aqueous environment, as alkoxides are stronger bases than the hydroxide and the reaction could also proceed in a reverse direction (at most, it can be said that the alkoxide is present in a transient form in an equilibrium reaction shifted towards the alcohol).

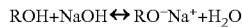
ROH+NaOH⇌RO⁻Na⁺+H₂O

This being stated, it has been unexpectedly found that, by properly dosing the quantity of aqueous alkali, it is equally possible to obtain a certain quantity of polyoxide residues (alkoxides), analogously to what happens in the general reaction of alcohols with metallic Na in an anhydrous environment (such as, for example, for the ethanol which forms sodium ethoxide, $CH_3$—$CH_2$—O⁻Na⁺).

Given the presence of activated ethylene alkyl groups (those of "monomers" with at least a pair of carbon-carbon double bonds, >C=C<,) these immediately react with the alkoxide groups of the polymer by opening the double bonds and forming cross-linked chains of an ether type in different points of the polymer/s itself.

Reactions of this type develop quite rapidly and in a way directly proportional to the temperature and the concentration of monomers (beside depending also on the length or molecular degree of the polymer/s and the quantity of existing soda) by giving the possibility of obtaining a very wide range of products with a structure having features which vary from the consistency of the hard rubber to the elastic one, to the one, always well bound, but as a mobile gel (precisely said hydrogel).

Just because of the reaction rate it is required to use, in case of the present invention, particularly precautions (namely, particularly reaction conditions) as the aforesaid high rate tends to cause, in the forming hydrogel mass, irregular cross-linking zones and, therefore, with a different consistency and viscosity from zone to zone.

This could involve the presence of non-uniformity within the structure of the final hydrogel which would be negatively reflected on its possibilities of use (for example, as for its features, such as injectability, patternability, aesthetic result throughout the duration of the prosthesis).

Conditions of the cross-linking reaction (for example, temperature adjustment, reaction time, stirring rate), as well as the choice of the type of polymer and/or monomers, will be selected by the skilled artisan as a function of the end product (specific for its desired use), his proven experience in the field, beside as a function of the common knowledges of the art.

By mere way of absolutely non limiting example, the choice of the monomer or monomers containing at least a pair of double bonds will be made by the skilled artisan as a function of their intrinsic reaction rate and their molecular weight, which contribute in a substantial way to the formation and the features of the end product.

According to a generally applicable procedure, an opportune quantity of non-pyrogen bi-distilled water is placed in a reactor having a reflux cooler and heating and stirring means, and is heated at a temperature between 70° C. and 100° C.; preferably, the temperature is between 80° C. and 95° C.; more preferably, is about 90° C. Then, under stirring, the desired quantity of completely hydrolized PVOH is slowly added and stirring and heating are maintained for a time on average between 1 h and 4 h (preferably, of about 2 h) until a clear and homogeneous solution is obtained.

The PVOH quantity, relative to the water, varies depending on the viscosity of the used PVOH and, above all, depending on the final dilution of the hydrogel which one desires to obtain (and, therefore, depending on its physical aspect; for example, if one desires to obtain a thicker, more gelatinous or even rubbery hydrogel, or, if one desires to obtain a more liquid end product).

Usually, PVOH is added in a weight percentage (g/g), relative to the water, between about 4% and about 25%; preferably, between 5% and 15% by weight.

In a preferred embodiment of the invention, PVOH is a PVOH completely hydrolized with a medium/medium-high density. Preferably, said PVOH is characterized by a molecular size (or molecular degree, corresponding to the number n of the hydroxyvinyl repeating units below reported) between about 1500 and about 2500. Preferably, the molecular size n is of about 2000.

—[$CH_2$—CHOH]$_n$—

Once the clear and homogeneous solution above described has been obtained, at least a monomer containing at least a pair of double bonds is added and the mixture is maintained under stirring (preferably, the stirring rate is decreased) until a complete dissolution of said at least one monomer.

The quantity of said at least one monomer above mentioned is greatly varying as a function of the interpolymer cross-linking degree which one desires to obtain.

Therefore, the skilled artisan will be able to freely select the type and quantity of monomer, depending on if he wishes to obtain final hydrogels more or less thick and/or more or less resistant (long lasting) to the hydrolytic action of the organism.

In a preferred embodiment of the invention, said at least one monomer above described is a bis-alkylamide (such as a bis-methyl/ethyl/isopropylalkylamide) with a pair of double bonds >C=C<; preferably, it is a bis-alkylacrylamide.

Preferably, said at least one monomer is added in a weight percent quantity (g/g), relative to PVOH, between 0.5% and 20%; preferably, from 2% to 10%; more preferably, from 3% to 10%.

To the solution thus obtained the desired quantity of aqueous basic solution is finally added and a slow stirring is maintained (for about 1-2 h) at a temperature between 60 and 70° C. Then, the temperature is further decreased at a value between 45° C. and 55° C., preferably at about 50° C., in about 20-30 minutes.

Preferably, the aforesaid basic solution consists of a 20% NaOH aqueous solution.

A hydrogel is obtained, which can have an appearance from very fluid (almost liquid) to very thick (almost rubbery), depending on the reaction conditions selected by the artisan who makes synthesis/formulations.

Said hydrogel has a basic pH, on average between 10 and 11.

Accordingly, the process above mentioned further includes a second step in which said hydrogel is washed with non-pyrogen water and neutralized. The operation requires much time, as the neutralization must occur in the whole mass under a slow and accurate stirring. Usually, the aforesaid neutralization step is carried out at a temperature close to the room temperature (for example, at a temperature between 25° C. and 45° C.; preferably, between 30° C. and 40° C.) by adding to the hydrogel obtained from the previous reaction step a quantity of non-pyrogen water of about 10 times the volume of the hydrogel itself and maintaining the mixture under a slow stirring until a complete neutralization.

If necessary, the neutralization step is repeated more times (for example, from 5 to 10 times) until the pH measured within the hydrogel reaches the neutrality.

Finally, the neutral product obtained is packaged and sterilized according to known techniques (for example at 121° C. for 20 minutes, or through gamma rays).

The process subject of the present invention is shown hereinbelow by mere way of absolutely non limiting example with respect to the various working variations which the skilled artisan can effect depending on the final results that he desires.

Example 1

In a reactor having a mechanical stirrer, reflux cooler and heating mantle, 800 g. of non-pyrogen bi-distilled water are placed and the temperature is brought to 90° C. Under stirring, 100 g. of completely hydrolized powdery PVOH, having a molecular degree of about 2000, are slowly added. Stirring and temperature are maintained until a clear and homogeneous solution is obtained.

At this point, with a reduced stirring rate, 3.8 g. of ethylene-bis-acrylamide are added and the stirring is maintained until a complete dissolution of the monomer. Finally, 30 g. of 20% NaOH are added and the mixture is slowly stirred for 1 h at 70° C.; after which, the temperature is decreased at 50° C. in about 30 minutes. A rubbery hydrogel at the concentration of about 13%, having pH of 10, is obtained.

The hydrogel is taken up 5 times with a quantity of non-pyrogen water corresponding to 10 times its volume and neutralized at pH=7 under a very slow stirring. The pH value is measured within the hydrogel.

Finally, the hydrogel is sterilized, after packaging, at 121° C. for 20 minutes.

Example 2

Following the procedure of the preceding example, the following is reacted:

| Non-pyrogen water | g. | 950 |
| Polyvinyl alcohol | g. | 50 |
| 20% NaOH | g. | 17.50 |
| Methylen-bis-acrylamide | g. | 3.50 |
| Ethylen-bis-acrylamide | g. | 1 |

In this case, after 2 h from the start of the processing, stirring and heating are stopped and the mixture is left on standing for 2 h; finally, it is placed in an oven at 50° C. for a time between 12 and 15 hours.

Neutralization is carried out at 30-40° C.

A hydrogel is obtained, having a concentration of 5%, characterized by viscosity and consistency lower than those of the Example 1.

The fluid product is packaged in a ready-to-use syringe and sterilized.

Hydrogels of the present invention appear as compounds having a remarkable structural homogeneity and a remarkable versatility of use.

Among the particular peculiarities of said products, it is worthwhile to particularly point out at least the following: the biodegradability, the biocompatibility, the complete non-toxicity.

As for the several application fields (i.e., uses) of hydrogels obtainable with the process of the present invention, the same find an advantageous employ as:
  medical device for an animal and/or human, or
  prosthesis for an animal and/or human, or
  carrier of drugs for an animal and/or human, or
  rays absorbers for an animal and/or human, or
  substitutes of hyaluronic derivatives, also for problems concerning joints, or
  antiparasitic agent vehicles in the plant field (for example, against the poplar woodworm and of the wood in general), or
  insoluble films and/or membranes with a gas-barrier effect.

In a particularly preferred embodiment of the invention, hydrogel of the present invention falls within the family of medical devices and is subcutaneously injected by specialists as a filler of soft parts and as in aestheticisms corrector in aesthetic surgery.

One of its preferred uses is therefore the one of filler which can be injected and patterned in loco after the application and is biodegradable in more or less long times, depending on the type of polymer and the type and the number of cross-linking monomers used for preparing the same.

Advantageously, the hydrogel obtainable with the method of the present invention perfectly meets the needs above pointed out, as:
  is free of residual monomers (of catalysts or collateral reaction products, such as dimers)
  maintains its own viscosity over time
  is degradable over time and biocompatible
  is bacteriologically pure has a neutral pH has a high hot wash-resistance in water allows to obtain several varieties of viscometric, elastomeric and time-resistance characteristics has homogeneous and constant viscosity and consistency corresponding with the type of application which has to be made in a medical field.

The innovation generated by the method of the present invention therefore allows to produce and provide the skilled artisan with a very wide range of homogeneous, stable and differently structured hydrogels, suitable for meeting the most different requirements.

The invention claimed is:

1. A method of using a cross-linked hydrogel, said cross-linked hydrogel obtained by a process in which the cross-linked hydrogel is obtained through a reaction step which consists of reacting a hydroxyl function-containing polymer selected from the group consisting of polyvinyl alcohol, polyallyl alcohol, and polyvinylethylene alcohols, with a monomer containing at least two carbon-carbon double bonds selected from the group consisting of bisacrylamides, methylenebisacrylamide, ethylenebisacrylamide, isopropylenebisacrylamide and diallyl urea, in an aqueous basic environment, said method comprising a step of using said hydrogel as an injectable filler for treating a joint tissue deficit.

2. The method according to claim 1, wherein said injectable filler can be injected and patterned in loco after the application.

3. The method according to claim 2, wherein said injectable filler is reabsorbable.

4. The method of claim 1, wherein the hydrogel is free of residual monomers of catalyst.

5. The method of claim 1, wherein the hydrogel is free of residual monomers of collateral reaction products.

6. The method of claim 4, wherein the hydrogel is free of residual monomers of collateral reaction products.

7. The method of claim 1, wherein said injectable filler is effective to be subcutaneously injected as a filler of soft parts.

* * * * *